United States Patent [19]
Schweitzer et al.

[11] Patent Number: 5,618,999
[45] Date of Patent: Apr. 8, 1997

[54] APPARATUS AND METHOD FOR MONITORING CONDITION OF OBJECTS

[75] Inventors: David P. Schweitzer, North Canton; James A. Grimes, Sr., Akron, both of Ohio

[73] Assignee: The Goodyear Tire & Rubber Company, Akron, Ohio

[21] Appl. No.: 536,504

[22] Filed: Sep. 28, 1995

[51] Int. Cl.$^6$ .................................................. G01M 19/00
[52] U.S. Cl. ........................... 73/866.5; 73/104; 73/1.01; 33/711; 33/744; 324/202; 198/810.02
[58] Field of Search ................. 73/866.5, 865.8, 73/865.9, 104, 146, 1 R, 1 J, 1 D, 1 DV, 635–641; 324/222, 223, 221; 33/711, 744, 745, 776; 198/810.01, 810.02, 810.03

[56] References Cited

U.S. PATENT DOCUMENTS

| | | | |
|---|---|---|---|
| 3,371,524 | 3/1968 | Wloszek | 73/1 DV X |
| 3,834,524 | 9/1974 | Retz et al. | 198/810.02 |
| 3,939,570 | 2/1976 | Loftus | 33/544.3 |
| 3,952,581 | 4/1976 | Gottelt | 73/640 |
| 3,956,632 | 5/1976 | Hall et al. | 198/810.03 X |
| 4,285,243 | 8/1981 | Collingwood | 73/639 X |
| 4,747,317 | 5/1988 | Lara | 73/866.5 X |
| 4,757,258 | 7/1988 | Kelly, Jr. et al. | 324/220 |
| 5,133,220 | 7/1992 | Alford et al. | 73/866.5 |
| 5,370,006 | 12/1994 | Zollinger et al. | 73/865.8 |
| 5,473,953 | 12/1995 | Appel | 73/635 X |

FOREIGN PATENT DOCUMENTS

| | | | |
|---|---|---|---|
| 106016 | 4/1992 | Japan | 198/810.02 |
| 24538 | 2/1994 | Japan | 198/810.02 |
| 2044929 | 10/1980 | United Kingdom | 73/639 |

OTHER PUBLICATIONS

Patent Abstracts of Japan "Central Hole Inspecting Apparatus for Turbine Rotor" Grp. p1748, vol. 18, No. 295 Abs Pub. date Jun. 6, 1994 (6–58850).

Primary Examiner—Thomas P. Noland
Attorney, Agent, or Firm—Marc R. Dion, Sr.; Roger D. Emerson

[57] ABSTRACT

An apparatus and method for monitoring the condition at or near the surface of objects is disclosed. The apparatus is a vehicle which includes a housing which is supported and translated across the object surface by three wheels. The front or first wheel is associated with an encoder and sensor which magnetically determines the physical condition of the object. The apparatus includes a starter block which includes a series of metallic wires embedded at certain depths and locations within the starter block. The vehicle passes over the starter block prior to passing over the object in order that the vehicle be recalibrated by the starter block prior to observing the physical condition of the object.

18 Claims, 6 Drawing Sheets

APPARATUS AND METHOD FOR MONITORING CONDITION OF OBJECTS

BACKGROUND OF THE INVENTION

This invention pertains to the art of methods and apparatus for monitoring the physical condition of an object. One application of the invention is articles incorporating metallic members, such as conveyor belts which are reinforced with cabled wires.

The present invention contemplates a new and improved method and apparatus for monitoring the condition of products reinforced with metallic reinforcements, such as conveyor belts reinforced with steel cables.

SUMMARY OF THE INVENTION

In accordance with the present invention, a new and improved method and apparatus for monitoring the condition of an object is provided.

More particularly, in accordance with one aspect of the invention, an apparatus for monitoring the condition of an associated article reinforced with metallic cords includes a vehicle having a housing having an interior and a bottom. The apparatus includes locomotion means for locomoting the vehicle across the associated article. The locomotion means are affixed to the bottom of the housing. The interior of the housing includes sensing means for sensing metallic cords in the associated article.

In accordance with another aspect of the invention, the apparatus includes an encoder means for measuring translational distance traveled by the apparatus.

According to another aspect of the invention, the apparatus includes a sensor which is associated with the encoder means and which is mounted inside a first wheel which is mounted on the housing.

According to another aspect of the invention, the apparatus includes a starting block which has several metallic members mounted therewithin. The housing selectively passes over the starting block before passing over the associated article, thereby the sensing means senses the first metallic member, and then other metallic members, in the starting block and is recalibrated before translating over the associated article.

According to another aspect of the invention, an apparatus for recalibrating an associated monitoring means from monitoring the location and condition of metallic cords in an associated article. The apparatus includes a body which has a top surface and a bottom surface and a thickness therebetween and a first metallic member mounted within the body. The first metallic member comprises a wire or cable. The apparatus further includes second, third, fourth and fifth metallic members, all mounted at specific locations different from the others.

According to a still further aspect of the invention, a method for monitoring the location and condition of metallic members within an associated article includes the steps of traversing a width of the associated article with a vehicle, sensing the location and condition of the metallic members in the associated article while the vehicle traverses the width of the associated articles, identifies an edge of the associated article, and stopping the vehicle at the edge of the associated article.

According to a further aspect of the invention, the method includes the step of calibrating the vehicle prior to traversing the width of the associated article, by traversing the vehicle over a starting block having metallic members embedded therewithin.

One advantage of the present invention is the provision of a new apparatus which can monitor the location and condition of metallic members within an article, such as the condition and location of metallic reinforcements within a conveyor belt.

Another advantage of the present invention is its automated nature, being able to recalibrate itself, travel the width of a conveyor belt gathering data, and return to a convenient location for the operator to pick up and move the apparatus to the next desired location.

Another advantage of the present invention is its portability, so that such apparatus is easily carried to and used at remote locations. Since one of the primary objects of the invention is the monitoring of conveyor belts, and since conveyor belts are often used at locations difficult to reach, the portability of the invention is a primary benefit.

Another advantage of the invention is the recalibration of the apparatus before every traversing of the belt. Such constant and systematic recalibration prevents "drift" and ensures accurate data. Still other benefits and advantages of the invention will become apparent to those skilled in the art to which it pertains upon a reading and understanding of the following detailed specification.

BRIEF DESCRIPTION OF THE DRAWINGS

The invention may take physical form in certain parts and arrangements of parts, a preferred embodiment of which will be described in detail in this specification and which will be illustrated in the accompanying drawings, which form a part hereof and wherein.

DESCRIPTION OF THE PREFERRED EMBODIMENT

Figure 1:
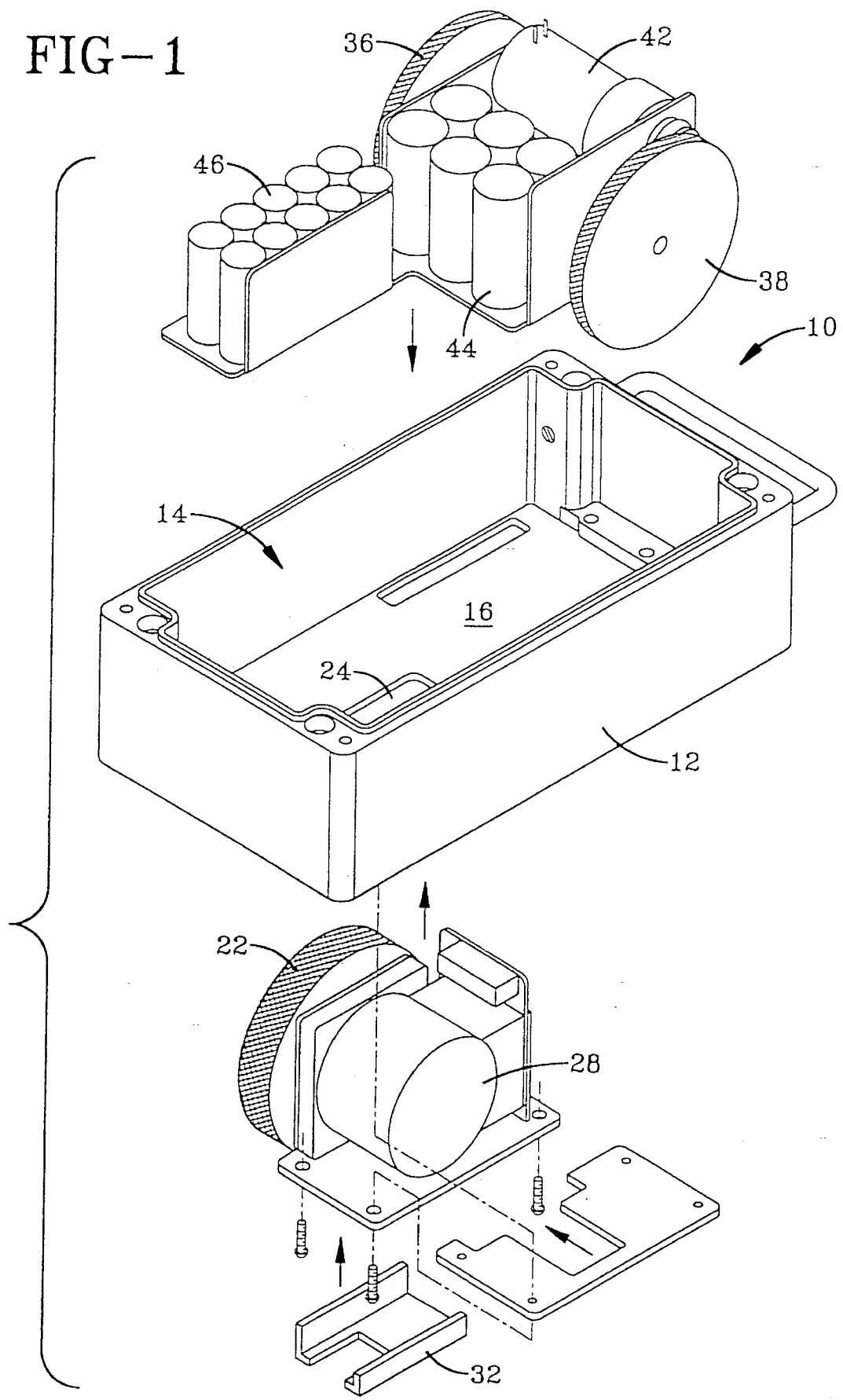
FIG. 1 is an exploded view of a vehicle according to the invention.
Figure 2:
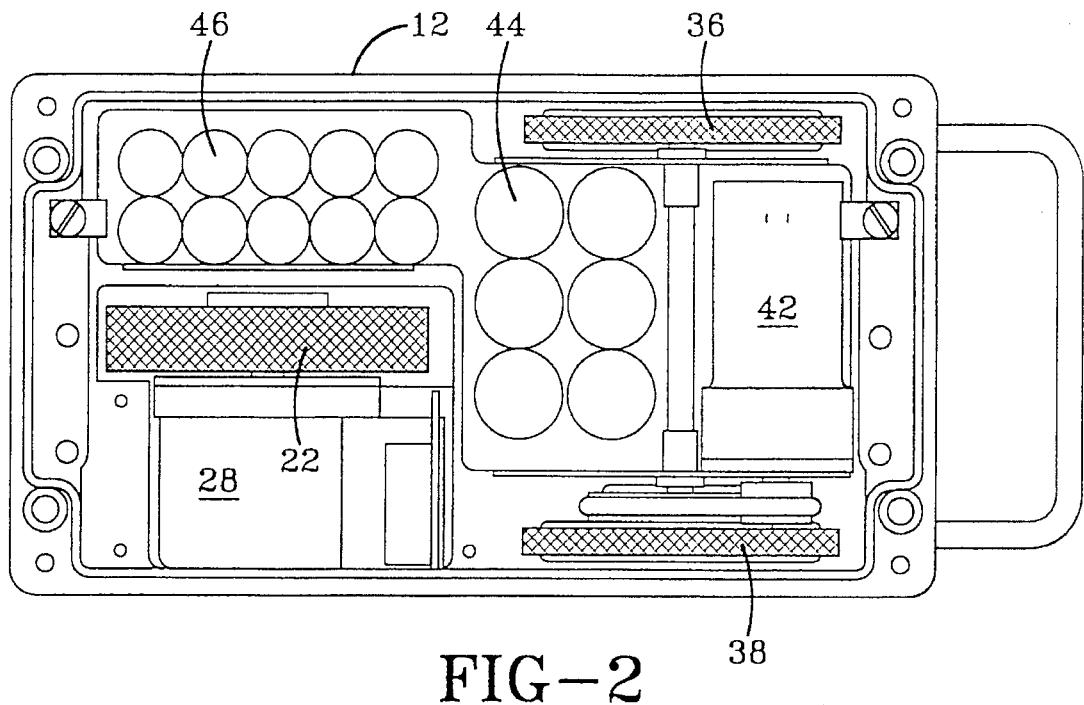
FIG. 2 is a top cross-sectional view of a vehicle according to the invention.
Figure 3:
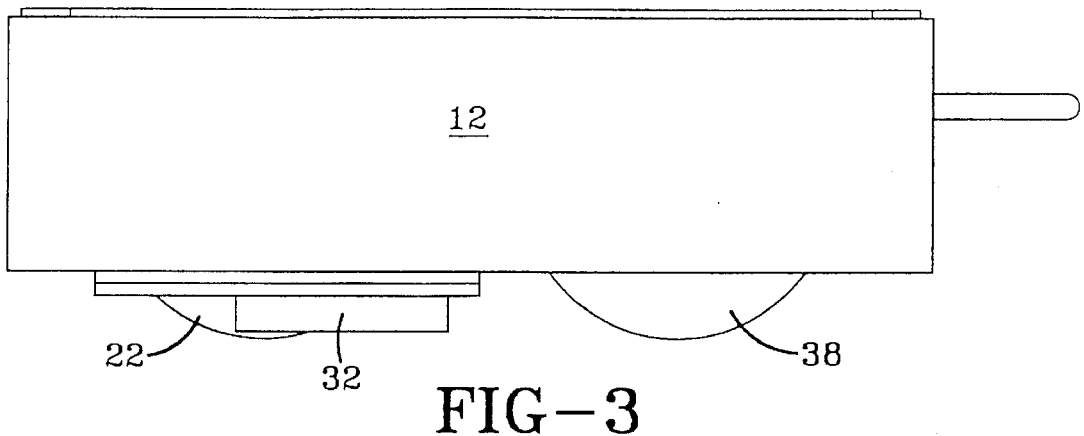
FIG. 3 is a side view of the vehicle shown in FIG. 2.
Figure 4:
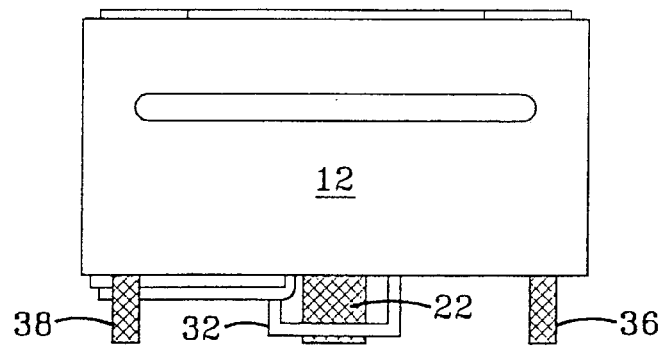
FIG. 4 is a rear view of the vehicle.

Referring now to the drawings wherein the showings are for purposes of illustrating a preferred embodiment of the invention only and not for purposes of limiting the same, FIG. 1 shows an exploded view of the primary components of a vehicle 10 according to the invention. The vehicle 10 includes a housing 12 which includes an interior 14 and a bottom surface 16. A front or first wheel 22 fits through a slot 24 in the bottom surface 16 of the housing 12. The first wheel 22 is made of aluminum and is operatively associated and connected to encoder means 28.

With reference to FIGS. 1–6 and 9, the encoder means 28 measures the distance the vehicle 10 travels across the width 78 of an associated conveyor belt 80. The first wheel 22 is also associated with a slide shoe 32, the operation of which will be discussed later. A sensor 62 is associated with the encoder means 28 and is mounted within the first wheel 22. The sensor 62 in the preferred embodiment is an Allegro microsystems model UGN3503 linear Hall effect sensor. For this application, the sensor 62 is magnetically driven with an Alnico-5 permanent magnet 94 which is 0.25 inches in diameter by 0.75 inches in length. While the preferred sensor 62 operates via the Hall effect, other physical characteristics and phenomena can be utilized to gather the desired information. The sensor 62 is epoxied to the end of the magnet 94. The encoder means 28 is mounted on an encoder shaft 30. The magnet 94 is mounted on a magnet/sensor mount 54.

While different sensors will work, the preferred sensor 62 is a Hall effect type sensor. As the sensor 62 senses the steel cables 81,82,83,84,85 in the starter block 70, the steel cables 81,82,83,84,85 which are closer to the axis of the magnet 94 increases the magnetic field coupling. This increased magnetic field coupling is sensed by the linear Hall effect sensor 62 and can be translated into the data desired. The centerline of the individual metallic cable 81,82,83,84,85 in question is at the peak of the signal. The horizontal position of the cable 81,82,83,84,85 is measured by the encoder when the peak occurs and is saved as the horizontal position of the cable. The amplitude of the signal at the peak is the depth of the cable 81,82,83,84,85 within the starter block 70.

One advantage of the encoder means 28 being connected to the front wheel 22 of the vehicle 10 is that the sensor 62 is positioned at the centerline of the vehicle 10 and inside the front wheel 22. By mounting the encoder means 28 and sensor 62 in this way, the magnetic field reaches through the aluminum front wheel and into the conveyor belt. The sensor 62 is not subject to mechanical abuse since it is mounted inside the first wheel 22 and close tracking is assured since the sensor 62 is just above the contact point of the front wheel 22.

With reference to FIGS. 1–6, also mounted within the interior 14 of the housing 12 are second and third wheels 36,38. Second and third wheels 36,38 are attached to a motor 42 which is powered by battery 44. Together with the second and third wheel 36,38, the motor 42 provides the locomotive means for translating the vehicle 10 across the width of a conveyor belt.

Figure 5:
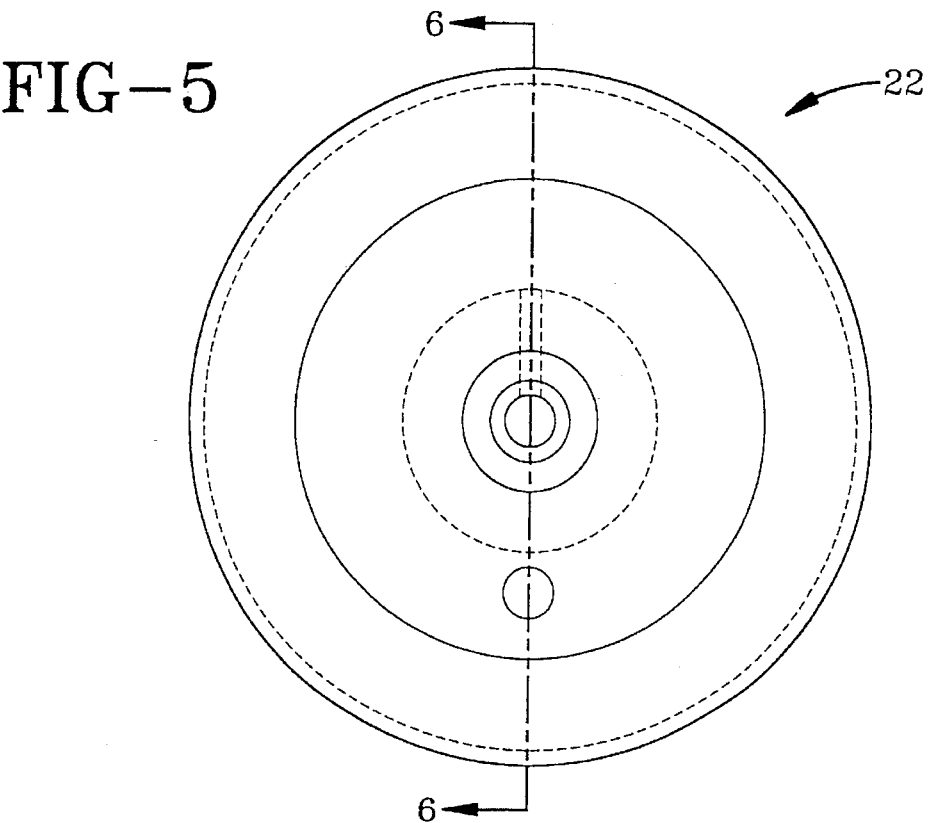
FIG. 5 is a side view of a front or first wheel of the invention.
Figure 6:
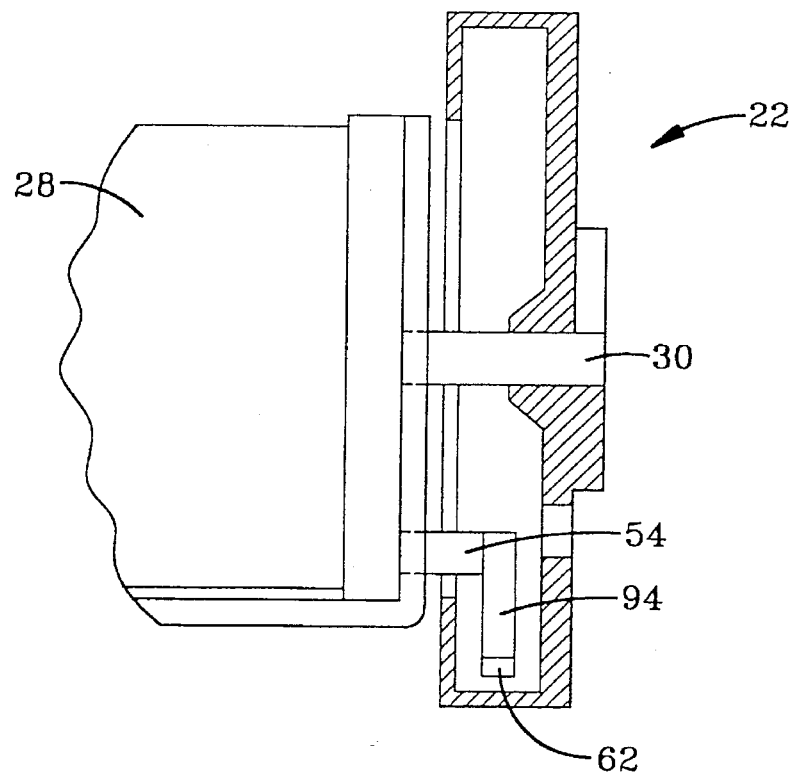
FIG. 6 is a cross-sectional view of the front or first wheel of the invention taken along line 6—6 of FIG. 5.

With reference to FIGS. 5 and 6, the first wheel 22 will be further discussed. First wheel 22 is essentially "C"-shaped in cross section and partially encloses an interior. Sensor 62 is located in the interior of first wheel 22 just above the contact point of the first wheel 22. While first wheel 22 rotates on encoder shaft 30, the sensor 62 remains in a fixed position above the contact point of the first wheel 22. In the preferred embodiment, the first wheel 22 is made of aluminum and has a 3 inch diameter and a width of about 0.63 inches.

Figure 7:
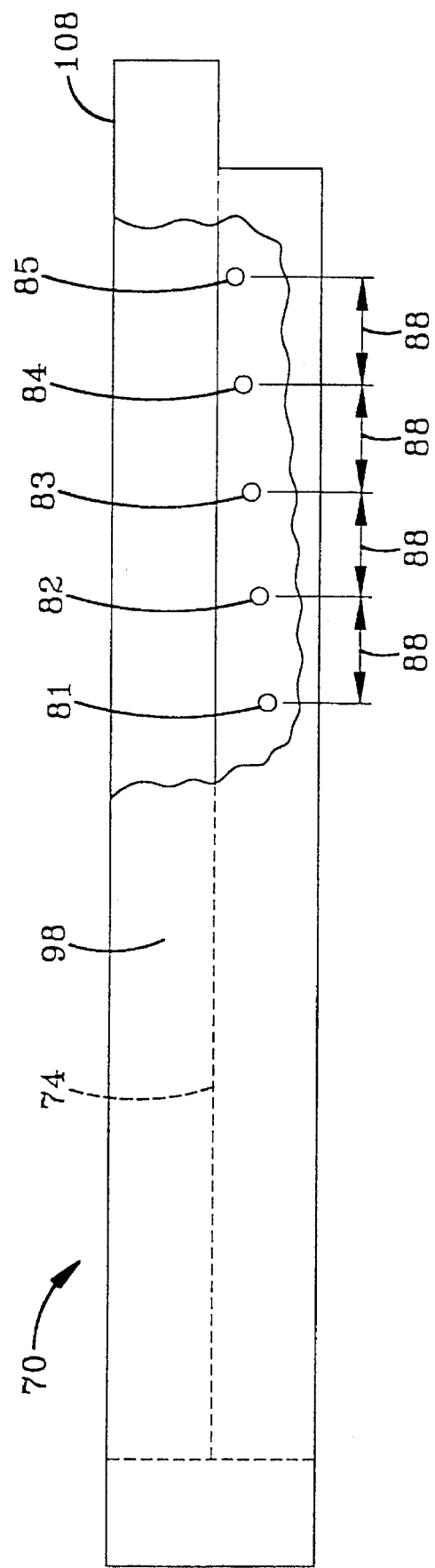
FIG. 7 is a side view of a starting block according to one aspect of the invention.
Figure 8:
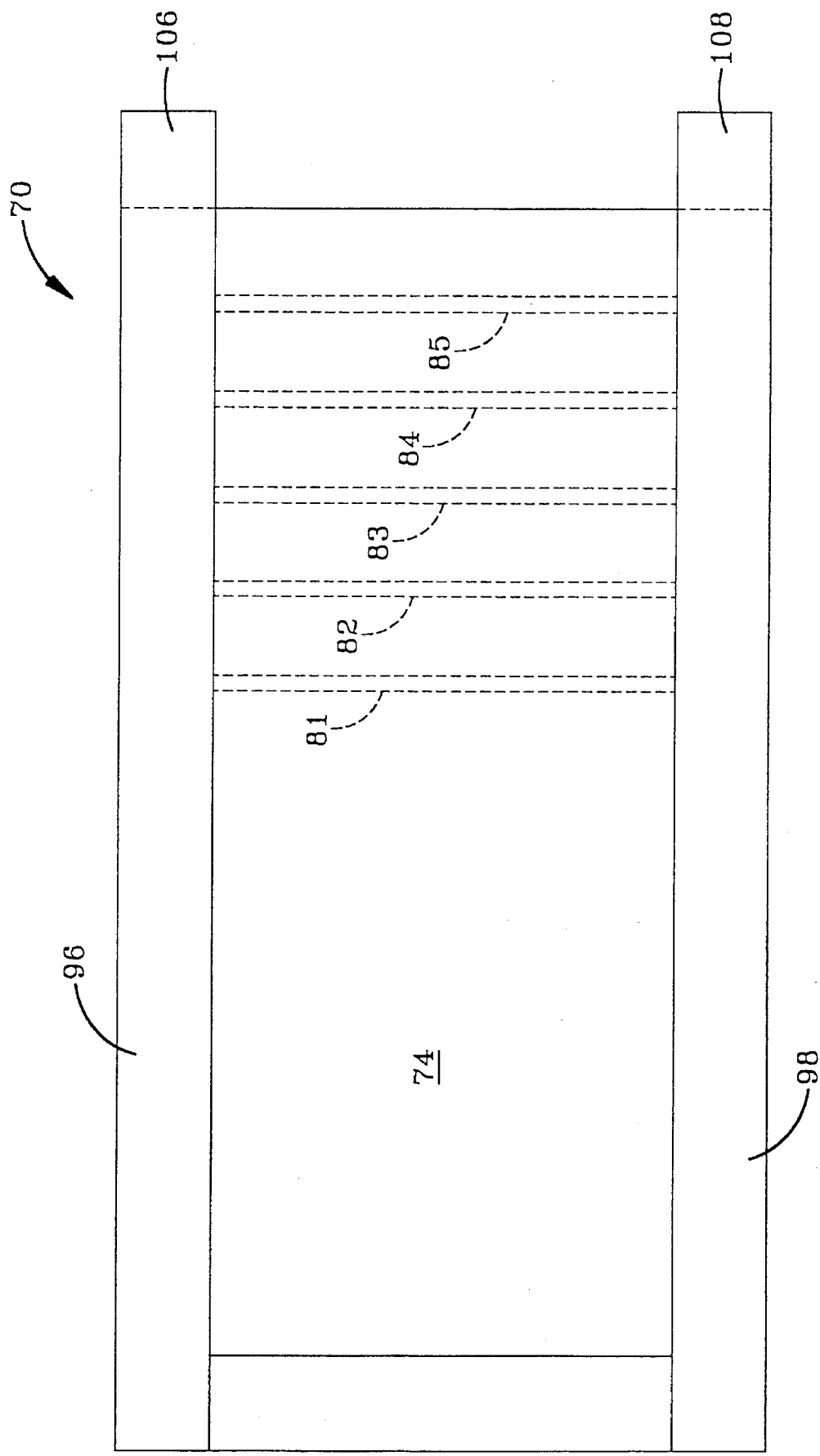
FIG. 8 is a top view of the starting block of FIG. 7.

With reference to FIGS. 7 and 8, another aspect of the invention will be described. A starter block 70 has a generally rectangular configuration. It is preferably made of elastomer, such as rubber. Its most distinguishing features are five wires embedded therein and their respective locations. First, second, third, fourth, and fifth wires 81,82,83, 84,85, are mounted within the starter block 70 and, as can be seen with reference to FIGS. 7 and 8, are separated by a fixed distance 88 along the width of the starter block 70. In the preferred embodiment, the fixed distance 88 is about 1 inch. With reference to FIG. 7, it can be seen that the wires 81,82,83,84,85 are also separated in the vertical dimension, meaning the respective wires 81,82,83,84,85 are embedded in the starter block 70 at different heights. As can be seen by reference to FIG. 7, the first wire 81 is lower than the other wires and the wires 81,82,83,84,85 are arranged in a "stair step" configuration.

By arranging the wires 81,82,83,84,85 in such a manner, the vehicle 10 can be recalibrated by simply passing it over a working surface 74 of the starter block 70. Because the wires 81,82,83,84,85 are placed in the starter block 70 at known locations, the data can be fed to the vehicle 10, allowing it to be recalibrated prior to measuring the actual article in question, such as a conveyor belt 80.

Figure 9:
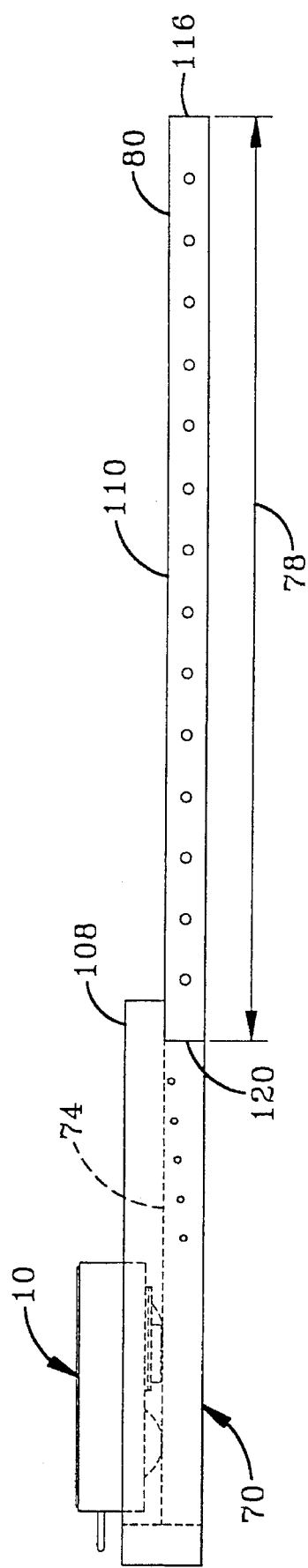
FIG. 9 is a schematic, cross-sectional view of the apparatus according to the invention.

With continuing reference to FIGS. 7–9, the starter block 70 further includes a working surface 74 which is bounded by first and second walls 96,98 respectively. The first and second walls 96,98 extend slightly above the plane of the working surface 74 to help guide the vehicle 10 forward onto the associated conveyor belt 80. One end of each of the walls 96,98 terminates in ears 106,108. The ears 106,108 fit over the top surface of the conveyor belt 80 so the working surface 74 of the starting block 70 is at essentially the same plane as the top surface of the conveyor belt 80.

The vehicle 10 disclosed above, when used in association with the starter block 70, provides a new method of monitoring the location and condition of metallic members within an associated article, such as the location and condition of metallic cords within a conveyor belt 80. The inventive method includes the steps of calibrating the vehicle 10 prior to traversing a width 78 of the associated article 80, with the calibration being accomplished by traversing the vehicle 10 over the starting block 70. Next the vehicle 10 traverses the width of the associated article, such as the conveyor belt 80. While doing so, the vehicle 10 rolls on first, second, and third wheels 22,36,38 until the first wheel 22 rolls off an edge 116 of the conveyor belt 80. By doing so, the edge 116 of the conveyor belt 80 is identified and the vehicle 10 stops progressing forward. When the first wheel 22 of the vehicle 10 rolls off the edge 116 of the conveyor belt 80, its speed goes to zero. A sealed bearing in the encoder means 28 does not permit the first or front wheel 22 to coast. When the speed of the first wheel 22 goes to zero, this event is detected by the encoder means 28. The computer is programmed to reverse the direction of the motor 42 upon such occurrence and the vehicle 10 progresses backward across the conveyor belt 80 a preset distance. The vehicle 10 traverses the conveyor belt 80 a second time in the reverse direction a distance shorter than the distance it traveled forward across the same conveyor belt 80. The return trip is shorter so that the vehicle 10 does not leave the other edge 120 of the conveyor belt 80 and again enter the starter block 70, but instead remains on the top surface 110 of the conveyor belt 80 at a location convenient for the operator.

When the first wheel 22 of the vehicle 10 rolls off the edge 116 of the conveyor belt 80, the slide shoe 32 prevents the vehicle 10 from tipping over.

The invention has been described with reference to a preferred embodiment. Obviously, modifications and alterations will occur to others upon a reading and understanding of this specification. It is intended to include all such modifications and alterations insofar as they come within the scope of the appended claims or the equivalents thereof.

Having thus described the invention, it is now claimed:

1. An apparatus for observing a physical condition of an associated object at or near a surface of the object, the apparatus comprising:

a vehicle including a housing, the housing having a bottom surface and an interior and locomotion means for locomoting the vehicle in a first direction across the surface of the object, the locomotion means comprising first, second and third wheels, the first wheel being toward a front end of the housing and being aligned with a centerline of the housing, the second and third wheels being near a rear end of the housing; and, a sensor for sensing the physical condition of the object, the sensor being located in an interior of the first wheel closely spaced from a contact point of the first wheel.

2. The apparatus of claim 1 wherein the second and third wheels are powered.

3. The apparatus of claim 1 wherein the first wheel is made of aluminum.

4. The apparatus of claim 1 further comprising:

encoder means for measuring a translational distance traveled by the vehicle, the encoder means being mounted in the interior of the housing.

5. The apparatus of claim 4 wherein said encoder means further comprises:

a sealed bearing to prevent the first wheel from coasting when a speed of the first wheel goes to zero.

6. The apparatus of claim 5 wherein said encoder means further comprises:

reversing means for reversing the direction of the housing when the speed of the first wheel goes to zero.

7. The apparatus of claim 14 further comprising:

a magnet mount attached at one end to the encoder means and extending to the interior of the first wheel;

a magnet for magnetically driving the sensor, the magnet being mounted to a distal end of the magnet mount, the sensor being affixed to the magnet.

8. The apparatus of claim 1 further comprising:

a starting block, the starting block having a working surface essentially in the same plane as the surface of the associated object and a first metallic member mounted therewithin at a first location within the starting block, the vehicle selectively passing over the starting block before passing over the surface of the associated object, the sensor sensing the first metallic member in the starting block and being recalibrated before the vehicle translates over the surface of the associated object.

9. The apparatus of claim 8 wherein the starting block further includes a second metallic member, the second metallic member being located within the starting block at a second location different from the first location of the first metallic member.

10. The apparatus of claim 8 wherein the starting block further comprises:

first and second walls on either side of the working surface, the first and second walls extending slightly above the plane of the working surface to guide movement of the vehicle in the first direction from the starting block onto the associated surface.

11. The apparatus of claim 10 wherein each of the first and second walls comprise an ear which engages the surface of the associated object to maintain the working surface of the starting block in the same plane as the surface of the associated object.

12. The apparatus of claim 8 wherein the starting block consists essentially of an elastomeric material apart from the metallic member mounted therein.

13. The apparatus of claim 1 wherein the bottom surface includes a slot aligned with the centerline of the housing and wherein the first wheel extends through the slot.

14. The apparatus of claim 1 further comprising:

a motor for driving the second and third wheels; and, a battery for powering the motor.

15. The apparatus of claim 1 further comprising:

a slide shoe located beneath the housing for preventing the vehicle from tipping over when the first wheel translates past an edge of the associated object.

16. The apparatus of claim 1 wherein the sensor is a linear Hall effect sensor.

17. An apparatus for observing a physical condition of an associated object at or near a surface of the object, the apparatus comprising:

a housing, the housing having an interior;

locomotion means for locomoting the housing across the object, the locomotion means being mounted in the housing, the locomotion means having only three wheels, a first wheel being toward a front end of the housing and being aligned with a centerline of the housing, a second and a third wheel being near a rear end of the housing; and, sensing means for sensing the physical condition of the object, the sensing means located within the first wheel.

18. The apparatus of claim 17 further comprising:

encoder means for measuring a translational distance traveled by the housing.

* * * * *